(12) United States Patent
Van Veen et al.

(10) Patent No.: US 12,402,853 B2
(45) Date of Patent: Sep. 2, 2025

(54) SYSTEMS AND METHODS FOR REAL-TIME VIDEO ENHANCEMENT

(71) Applicant: Subtle Medical, Inc., Menlo Park, CA (US)

(72) Inventors: David Van Veen, San Francisco, CA (US); Long Wang, Sunnyvale, CA (US); Ben Andrew Duffy, Mountain View, CA (US); Enhao Gong, Sunnyvale, CA (US); Tao Zhang, Menlo Park, CA (US)

(73) Assignee: SUBTLE MEDICAL, INC., Menlo Park, CA (US)

( * ) Notice: Subject to any disclaimer, the term of this patent is extended or adjusted under 35 U.S.C. 154(b) by 372 days.

(21) Appl. No.: 17/880,831

(22) Filed: Aug. 4, 2022

(65) Prior Publication Data

US 2023/0038871 A1    Feb. 9, 2023

Related U.S. Application Data

(63) Continuation of application No. PCT/US2021/017189, filed on Feb. 9, 2021.
(Continued)

(51) Int. Cl.
*G06T 5/00* (2024.01)
*A61B 6/00* (2006.01)
(Continued)

(52) U.S. Cl.
CPC ............ *A61B 6/542* (2013.01); *A61B 6/5258* (2013.01); *G06T 5/50* (2013.01); *G06T 5/70* (2024.01);
(Continued)

(58) Field of Classification Search
CPC ..... A61B 6/542; A61B 6/5258; A61B 6/4441; A61B 6/486; A61B 6/487; A61B 6/5205;
(Continued)

(56) References Cited

U.S. PATENT DOCUMENTS 6,084,981 A    7/2000  Horiba et al.
6,314,160 B1   11/2001 Dhawale et al.
(Continued)

FOREIGN PATENT DOCUMENTS

CN    107610195 B    2/2021
EP    2356940 A1     8/2011
(Continued)

OTHER PUBLICATIONS

Zhang et al.: Hybrid 3D/2D-Based Deep Convolutional Neural Network for Spatio-Temporal Denoising of Angiography. ISICDM 2019: Proceedings of the Third International Symposium on Image Computing and Digital Medicine pp. 157-160.
(Continued)

*Primary Examiner* — Iriana Cruz
(74) *Attorney, Agent, or Firm* — WILSON SONSINI GOODRICH & ROSATI

(57) ABSTRACT

A computer-implemented method is provided for improving live video quality. The method comprises: acquiring, using a medical imaging apparatus, a stream of consecutive image frames of a subject, and the stream of consecutive image frames are acquired with reduced amount of radiation dose; applying a deep learning network model to the stream of consecutive image frames to generate an image frame with improved quality; and displaying the image frame with improved quality in real-time on a display.

18 Claims, 7 Drawing Sheets

Related U.S. Application Data

(60) Provisional application No. 62/972,999, filed on Feb. 11, 2020.

(51) Int. Cl.
   *G06T 5/50* (2006.01)
   *G06T 5/70* (2024.01)
   *G06V 10/82* (2022.01)

(52) U.S. Cl.
   CPC .... *G06V 10/82* (2022.01); *G06T 2207/10016* (2013.01); *G06T 2207/10121* (2013.01); *G06T 2207/20081* (2013.01); *G06T 2207/20084* (2013.01); *G06T 2207/20216* (2013.01); *G06T 2207/30004* (2013.01); *G06T 2207/30168* (2013.01)

(58) Field of Classification Search
   CPC ........... A61B 6/5264; G06T 5/50; G06T 5/70; G06T 2207/10016; G06T 2207/10121; G06T 2207/20081; G06T 2207/20084; G06T 2207/20216; G06T 2207/30004; G06T 2207/30168; G06T 5/60; G06T 2200/24; G06T 2207/10081; G06T 2207/10088; G06T 2207/10104; G06T 2207/10108; G06T 2207/20182; G06V 10/82; G06V 2201/03; G06F 18/24137
   See application file for complete search history.

(56) References Cited

U.S. PATENT DOCUMENTS

| | | | |
|---|---|---|---|
| 2009/0225940 A1* | 9/2009 | Aoyama | A61B 6/503 378/62 |
| 2016/0335754 A1* | 11/2016 | Aaron | H04N 21/4666 |
| 2017/0014094 A1* | 1/2017 | Hiroshige | A61B 6/54 |
| 2018/0235557 A1* | 8/2018 | Rousso | A61B 8/4416 |
| 2019/0035118 A1 | 1/2019 | Zhao et al. | |
| 2019/0139205 A1* | 5/2019 | El-Khamy | G06V 30/2504 |
| 2019/0347772 A1 | 11/2019 | Zhang et al. | |
| 2019/0371450 A1* | 12/2019 | Lou | G16H 50/30 |
| 2021/0160556 A1* | 5/2021 | Jang | H04N 21/435 |
| 2022/0156884 A1* | 5/2022 | Kemp | G06T 3/4046 |

FOREIGN PATENT DOCUMENTS

| | | |
|---|---|---|
| WO | WO-2002056770 | 7/2005 |
| WO | WO-2019019199 A1 | 1/2019 |
| WO | WO-2021163022 A1 | 8/2021 |

OTHER PUBLICATIONS

Balter, et al., "Fluoroscopically guided interventional procedures: a review of radiation effects on patients' skin and hair," Radiology, vol. 254, No. 2, pp. 326-341, 2010.

Davy et al. Non-local video denoising by CNN. arXiv preprint arXiv:1811.12758. pp. 1-14 (2018).

Dosovitskiy, et al., "Flownet: Learning optical flow with convolutional networks," in Proceedings of the IEEE international conference on computer vision, 2015, pp. 2758-2766.

Grace et al. Retrospective Analysis: Collateral nerve damage and local tissue trauma associated with endovenous laser ablation therapy. International Journal of Scientific and Research Publications Submission. (2018) Available at https://docs.google.com/document/d/e/2PACX-1vQnU5wYkr4eqtjFatBkgDOGjM7PbfTmhX2LC9fhKqjiOSWYgX0m3W_jnL2P7WPF3uRh4OjkXEuv0Lo7/pub.

Hoffman, et al., "Breast cancer in women with scoliosis exposed to multiple diagnostic x rays," JNCI: Journal of the National Cancer Institute, vol. 81, No. 17, pp. 1307-1312, 1989.

Huda, Walter, "Kerma-area product in diagnostic radiology," American Journal of Roentgenology, vol. 203, No. 6, pp. W565-W569, 2014.

Kingma, et al. Adam: A Method for Stochastic Optimization. Published as a conference paper at the 3rd International Conference for Learning Representations, San Diego, 2015.

Krizhevsky. Imagenet classification with deep convolutional neural networks. In Advances in neural information processing systems (pp. 1097-1105) 2012.

Maggioni et al. Video denoising, deblocking, and enhancement through separable 4-D nonlocal spatiotemporal transforms. IEEE Transactions on image processing, 21(9), 3952-3966 (2012).

Mastrangelo, et al. "Increased cancer risk among surgeons in an orthopaedic hospital," Occupational Medicine, vol. 55, No. 6, pp. 498-500, 2005.

Pazke et al. Automatic differentiation in pytorch. 31st Conference on Neural Information Processing Systems (NIPS 2017); pp. 1-4 (2017).

PCT/US20/17189 International Search Report and Written Opinion dated Apr. 23, 2021.

Primak, et al., "Relationship between noise, dose, and pitch in cardiac multi-detector row ct," Radiographics, vol. 26, No. 6, pp. 1785-1794, 2006.

Radiation Term: ALARA; Acronym Index. Health Physics Society, https://hps.org/publicinformation/radterms/radfact1.html. Retrieved from website on Mar. 4, 2020.

Rampersaud, et al., "Radiation exposure to the spine surgeon during fluoroscopically assisted pedicle screw insertion," Spine, vol. 25, No. 20,pp. 2637-2645, 2000.

Ronneberger et al. U-net: Convolutional networks for biomedical image segmentation. In International Conference on Medical image computing and computer-assisted intervention, pp. 234-241(2015).

Sampat, et al., "Complex wavelet structural similarity: A new image similarity index," IEEE transactions on image processing, vol. 18, No. 11, pp. 2385-2401, 2009.

Slovis, Thomas, "Children, computed tomography radiation dose, and the as low as reasonably achievable (alara) concept," Pediatrics, vol. 112, No. 4, pp. 971-972, 2003.

"Surgery Treatment." Dedicated Computing, https://www.dedicatedcomputing.com/markets/healthcare/surgery-treatment/ (2020).

Tassano et al. Dvdnet: A Fast Network for Deep Video Denoising. 2019 IEEE International Conference on Image Processing (ICIP) (pp. 1805-1809). IEEE (2019).

Tassano et al. FastDVDnet: Towards Real-Time Video Denoising Without Explicit Motion Estimation. arXiv preprint arXiv: 1907.01361. pp. 1-10 (2019).

Wu, et al., "Deep high dynamic range imaging with large foreground motions," in Proceedings of the European Conference on Computer Vision (ECCV), 2018, pp. 117-132.

Zhou, et al., "Minimally invasive surgery under fluoro-navigation for anterior pelvic ring fractures," Indian journal of orthopaedics, vol. 50, No. 3,pp. 250, 2016.

* cited by examiner

SYSTEMS AND METHODS FOR REAL-TIME VIDEO ENHANCEMENT

CROSS-REFERENCE TO RELATED APPLICATION

This application is a Continuation of International Application No. PCT/US2021/017189 filed on Feb. 9, 2021, which claims priority to U.S. Provisional Application No. 62/972,999 filed on Feb. 11, 2020, the content of which is incorporated herein in its entirety.

BACKGROUND

Image-guided surgery systems have been utilized to inspect patient anatomy or guide surgical instruments during surgical operations. These vision or image-guided systems may provide real-time vision feedback of the surgeon's movements, target site location, and various other useful information which can be displayed in real-time on computer monitors in the operating room or remotely.

Imaging modality such as C-arm fluoroscopy may provide in vivo real-time imaging in conjunction with ionizing radiation. In some cases, fluoroscopy imaging and other imaging systems may be provided to intraoperative interactive surgery planning and display systems, mixing live video of the external surface of the patient with interactive computer-generated models of internal anatomy obtained from medical diagnostic imaging data of the patient. The computer images and the live video are coordinated and displayed to a surgeon in real time during surgery, allowing the surgeon to view internal and external structures and the relationship between them simultaneously, and adjust the surgery accordingly. This may allow for safer and less invasive procedures as the surgeons have greater control of the procedure, hence reducing tissue trauma and disruption. However, fluoroscopic imaging relies on ionizing radiation to provide physicians with high quality video feedback during surgical operation. Radiation exposure is harmful for both physicians and patients, but reducing dosage can result in a noisier video. In some cases, in order to achieve live imaging with sufficient video quality, a patient may receive high dose radiation (e.g., continuous stream of x-rays) such that the absorbed dose of radiation in fluoroscopic imaging is typically greater than that of traditional still radiographs.

SUMMARY

Methods and systems are provided for enhancing quality of live video with low radiation dose. Methods and systems of the present disclosure may provide high-quality live video taken at lower dose of radiation without sacrificing video quality. The methods and systems provided herein may address various drawbacks of conventional systems, including those recognized above. Methods and systems of the present disclosure may be capable of improving live video quality in real-time thereby allowing for videos taken with lower radiation dose, or reduced exposure to radiation during imaging. This may beneficially improve operation safety to both patient and surgeon, as well as allow for long duration surgical operations (e.g., interventional procedures such as placing stents or other devices inside the body may which require fluoroscopy be administered for a long period of time).

Methods and systems provided herein may provide high-quality live video while lowering radiation dose. Traditionally, reducing the radiation dose or reducing radiation exposure may lead to noisier image frames or temporal artifacts with degraded video quality. Methods and systems of described herein, may improve the quality of the live medical imaging under lower radiation dose without modification to the physical system.

The provided methods and systems may significantly improve live video quality by applying deep learning techniques so as to improve video resolution and reduce noise. Methods or algorithms herein may improve live imaging quality with reduced inference runtime. This beneficially allows for real-time imaging enhancement that was not previously available due to the high inference runtimes of the conventional denoiser. Various video artifacts such as temporal artifacts (e.g., visible flickering), image artifacts such as noise (e.g., low signal noise ratio), blur (e.g., motion artifact), shading (e.g., blockage or interference with sensing), missing information (e.g., missing pixels or voxels in painting due to removal of information or masking), and/or reconstruction (e.g., degradation in the measurement domain) may be mitigated by the provided methods and systems.

In an aspect, the present disclosure provides a computer-implemented method for improving live video quality. The method comprises: (a) acquiring, using a medical imaging apparatus, a stream of consecutive image frames of a subject, where the stream of consecutive image frames is acquired with reduced amount of radiation dose; (b) applying a deep learning network model to the stream of consecutive image frames to generate an output image frame with an improved quality in both temporal domain and spatial domain; and (c) displaying the output image frame with the improved quality in real-time on a display.

In a related yet separate aspect, the present disclosure provides a non-transitory computer-readable storage medium including instructions that, when executed by one or more processors, cause the one or more processors to perform operations. The operations comprise: a) acquiring, using a medical imaging apparatus, a stream of consecutive image frames of a subject, where the stream of consecutive image frames is acquired with reduced amount of radiation dose; (b) applying a deep learning network model to the stream of consecutive image frames to generate an output image frame with an improved quality in both temporal domain and spatial domain; and (c) displaying the output image frame with the improved quality in real-time on a display.

In some embodiments, the deep learning network model is trained using training datasets comprising a pair of a simulated low-quality video and a simulated high-quality video. In some cases, the simulated high-quality video is generated by applying a temporal averaging algorithm or a denoising algorithm to a video acquired with a normal radiation dose. In some instances, the method further comprises computing a noise based on a difference between the video and the simulated high-quality video. Alternatively, the method further comprises applying a factor to the noise to simulate a level of noise corresponding to the factor. For example, the simulated low-quality video is generated based at least in part on the level of noise and the simulated high-quality video.

In some embodiments, the deep learning network model comprises a plurality of denoising components. In some cases, the plurality of denoising components are assembled in a two-layer architecture. In some instances, each denoising component in a first layer of the two-layer architecture processes a subset of the stream of consecutive frames to output a series of intermediate image frames with an enhanced image quality. In some cases, a denoising component in the second layer of the two-layer architecture processes the intermediate image frames with the enhanced image quality and generates the output image frame. In some cases, each denoising component includes a modified U-net model. In some instances, a denoising component in a second layer of the two-layer architecture has weights different from the weights of a denoising component in the first layer. In some embodiments, the medical imaging apparatus is performing fluoroscopic imaging.

Additionally, methods and systems of the disclosure may be applied to existing systems without a need of a change of the underlying infrastructure. In particular, the provided methods and systems may improve live imaging at no additional cost of hardware component and can be deployed regardless of the configuration or specification of the underlying infrastructure.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and descriptions are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
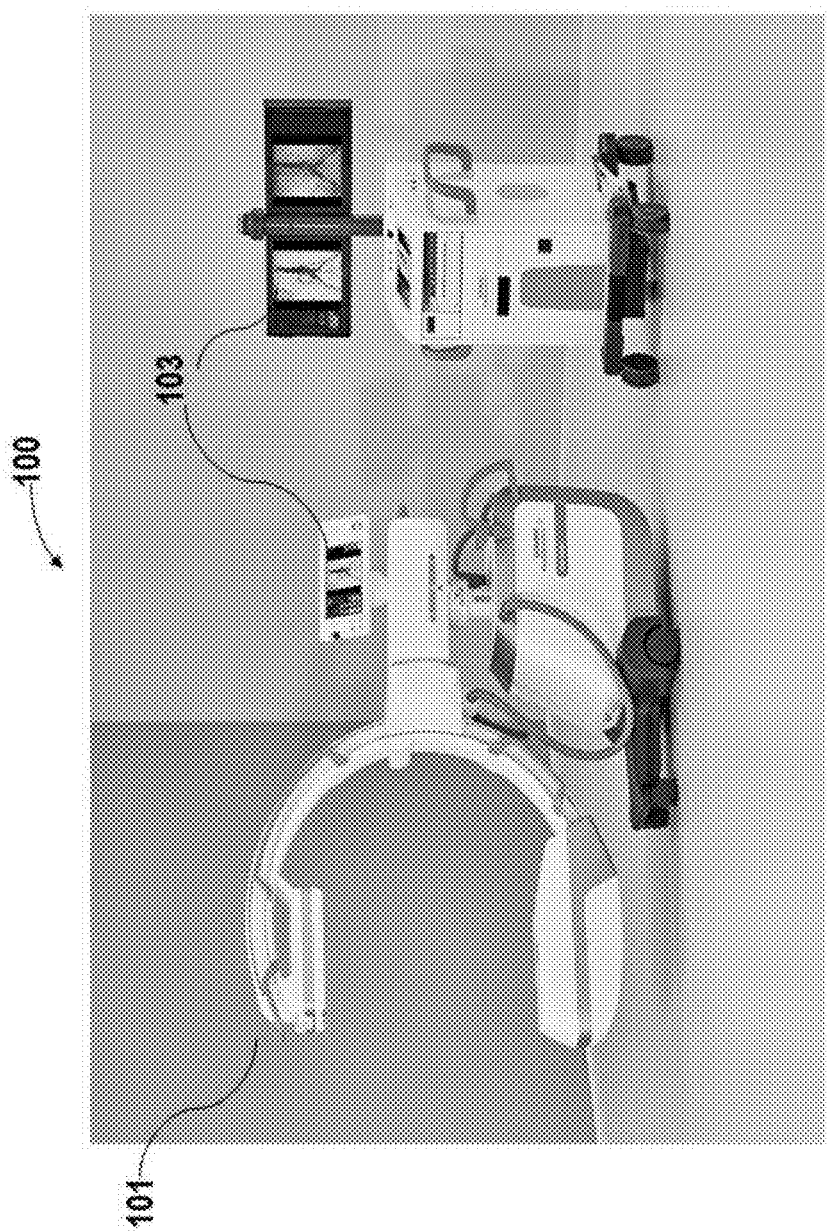
FIG. 1 schematically illustrates an example imaging system, in accordance with some embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure provides systems and methods that are capable of improving live medical video quality. In particular, the provided systems and methods may employ a deep learning framework that can perform real-time video quality enhancement during live video acquisition. The deep learning framework can also be used to reduce radiation dose levels while maintaining live video quality. This beneficially provides high-quality, real-time visual feedback to a surgeon during surgical operations with reduced exposure to radiation.

The provided systems and methods may enhance video quality in real-time in various aspects. Examples of low quality in live medical imaging may include noise (e.g., low signal noise ratio), low spatial resolution, temporal artifacts (e.g., visible flickering), contrast, blur (e.g., motion artifact), shading (e.g., blockage or interference with sensing), missing information (e.g., missing pixels or voxels due to removal of information or masking), reconstruction (e.g., degradation in the measurement domain), and/or under-sampling artifacts (e.g., under-sampling due to compressed sensing, aliasing).

In some cases, the provided systems and methods may employ a deep learning framework to improve the live imaging quality such as real-time video denoising to reduce ionizing radiation exposure. Systems and methods of the present disclosure can be applied to various live imaging modalities such as fluoroscopic imaging, computed tomography (CT), single photon emission computed tomography (SPECT) scanners, functional magnetic resonance imaging (fMRI), or magnetic resonance imaging (MRI) scanners, Positron Emission Tomography (PET) and various others. Though fluoroscopic imaging and ionizing radiation examples are primarily provided herein, it should be understood that the present approach may be used in other imaging modality contexts as described elsewhere herein.

The term "video quality" of surgical imaging may generally refer to the presence of the various live imaging artifacts that may affect the visual effect as described above (e.g., noise, contrast, missing information, low spatial solution, temporal artifacts such as flickering, etc.), or accuracy of imaging (e.g., accuracy of quantitative biomarker assessment). For example, video with high video quality may generally refer to video with low level of video artifacts whereas as low video quality may refer to high level of video artifacts. Various predictors, such as signal to noise ratio (SNR), contrast, sharpness, spatial/temporal resolution and the like, can be employed for qualifying the video quality.

The term "real-time," as used herein, generally refers to a response time of less than 1 second, tenth of a second, hundredth of a second, a millisecond, or less, such as by a computer processor. Real-time can also refer to a simultaneous or substantially simultaneous occurrence of a first event with respect to occurrence of a second event.

The term "reduced radiation dose" as utilized herein may refer to an amount or level of radiation dose that is lower than the amount/level of radiation dose (e.g., normal radiation dose) which is utilized for live imaging in order to achieve adequate quality in absent of the provided systems and methods. For example, the provided methods and systems may be capable of reducing the radiation dose by at least 10%, 20%, 30%, 40%, 50%, 60%, 70%, 80%, or 90% without lowing the quality the video or live imaging.

The provided systems and methods may be capable of achieving real-time video enhancement by performing image frame enhancement in no more than 60 millisecond, 50 millisecond, 40 millisecond, 30 millisecond, 20 millisecond, at a frame rate of at least 10 frame per second, 20 frame per second, 30 frame per second, 40 frame per second, 50 frame per second, thereby avoiding latency. In some cases, systems and methods of the present disclosure may be capable of achieving real-time video enhancement in no more than 33.3 millisecond or 12 millisecond, at 30 frames per second and 1536×1536 image resolution.

The image resolution may be dependent on the imaging sensor of the imaging system. The imaging sensor may be capable of capturing an image frame or a sequence of image frames at a specific image resolution. The image frame resolution may be defined by the number of pixels in a frame. The image resolution may be greater than or equal to about 352×420 pixels, 480×320 pixels, 720×480 pixels, 1280×720 pixels, 1440×1080 pixels, 1920×1080 pixels, 2048×1080 pixels, 3840×2160 pixels, 4096×2160 pixels, 7680×4320 pixels, 1536×1536, or 1536×8640 pixels. The imaging device may be, for example, a 4K camera or a camera with a higher resolution.

The imaging sensor may capture a sequence of image frames at a specific capture rate. In some cases, the sequence of images may be captured at standard fluoroscopic video frame rates such as about 25 frames per second or 30 frames per second. In some cases, the sequence of images may be captured at a rate less than or equal to about the standard frame rate while the temporal resolution of the video may be improved by the present methods and systems (e.g., interpolating across frames for smoother motion or reduce visible flicker).

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The provided systems and methods may beneficially allow for live image acquisition under reduced radiation dose or low radiation exposure with improved video quality. As described above, fluoroscopy is a type of medical imaging that shows a continuous X-ray image on a monitor, much like an X-ray movie. During a fluoroscopy procedure, an X-ray beam is passed through the patient body. The image is transmitted to a display so the movement of a body part or of an instrument or contrast agent ("X-ray dye") through the body can be seen in detail. The radiation dose that the patient receives varies depending on the individual procedure. Fluoroscopy can result in relatively high radiation doses, especially for complex interventional procedures (such as placing stents or other devices inside the body) which require fluoroscopy be administered for a long period of time. Fluoroscopic imaging taken under reduced radiation dose and/or low frame rate (e.g., low temporal resolution) may result in low video quality (e.g., high noise, low resolution, low contrast, visible flicker). Methods and systems of described herein, may improve the quality of the live medical image in real-time while allowing for reduced radiation dose without modification to the physical system (e.g., hardware configuration or set up).

Methods and systems provided herein may be capable of improving the quality of live medical imaging in real-time by utilizing a deep learning enhancement mechanism. Conventional denoising methods may employ deep learning to improve quality of a single-frame image such as improve resolution in the spatial domain within a single image frame. However, the conventional deep learning methods may not be applicable for live imaging or real-time imaging quality enhancement due to the high runtime for inference. For example, one family of solutions for video denoising are patch-based algorithms which construct 3D spatiotemporal volume by tracking blocks along motion trajectories with similar blocks, thus leveraging non-local spatial correlation as a fourth dimension. A second family of solutions to video denoising consists of deep learning methods such an end-to-end trained neural network which performs spatial denoising, frame warping, and temporal denoising in subsequent steps. However, the primary issue with both the patch-based and neural network methods is that they require an explicit stage of motion estimation or compensation. Performing explicit motion estimation and/or motion compensation can be computationally expensive which prohibit real-time denoising capability.

Methods and systems herein may adopt an improved deep learning framework or deep learning enhancement mechanism that advantageously provides real-time imaging quality enhancement. In some embodiments, the deep learning enhancement mechanism may improve live imaging quality by leveraging intraframe information in conjunction with interframe information. The output of the deep learning enhancement mechanism may be image stream with improved quality in at least one of noise, contrast, spatial resolution, and temporal resolution (e.g., smoothing motion, reducing flickering, interpolating across frames for smoother motion).

In some embodiments, the deep learning enhancement mechanism may be implemented by a convolutional neural network with rapid video denoising capabilities. In some cases, the enhancement mechanism may comprise a modified U-Net framework such as Fast Deep Video Denoising network (DVDnet). Details about the deep learning enhancement mechanism are described later herein.

System Overview

The systems and methods can be implemented on an existing imaging system such as but not limited to fluoroscopic imaging systems without a need of a change of hardware infrastructure. FIG. 1 schematically illustrates an example imaging system 100, in accordance with some embodiments. In the illustrated example, the imaging system 100 may comprise an imaging device (e.g. a C arm or O arm fluoroscopic imaging system) 101 to capture intraoperative live images. The imaging device 101 can utilize any suitable imaging modalities for capturing live video of a patient that may involve continuous radiation exposure of the patient and surgeon. The imaging system may be, for example, C-arm image intensifier or O-arm intraoperative CT. For instance, high-resolution X-ray images may be captured by the C-arm imaging scanner 101 in real-time, thus allowing the physician to monitor progress and immediately make any corrections. The C-arm fluoroscopy system may comprise a generator and X-ray image intensifier that converts x-rays into visible light at higher intensity than mere fluorescent screens do. The generator emits X-rays that penetrate the patient's body. The image intensifier or detector converts the X-rays into a visible image displayed on the monitor or other display of the imaging system 103.

In one aspect of the disclosure, a deep learning-based live imaging enhancement system may be provided to the imaging system 100 to improve the quality of the video in real-time. Quality of the live video may be improved in real-time such that the physician or surgeon may view the improved video on the display 103 without time delay.

Figure 2:
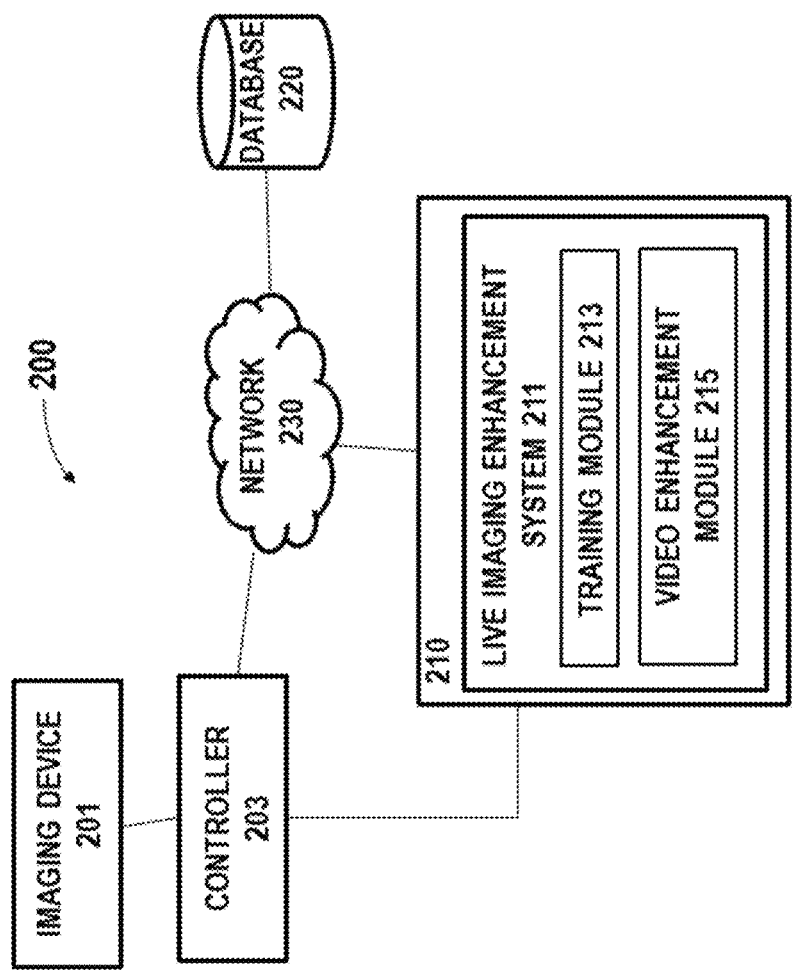
FIG. 2 schematically illustrates a live imaging enhancement system implemented in an imaging platform for real-time video enhancement, in accordance with some embodiments of the disclosure.

FIG. 2 schematically illustrates a live imaging enhancement system 211 implemented on an imaging platform 200 for real-time video enhancement. Video enhancement may be performed in real-time during surgical operations. For instance, quality of image frames may be improved in real-time as image frame being captured by the imaging device 201. Additionally, video enhancement may be performed at any desired time point after a video has been captured. The imaging platform 200 may comprise a computer system 210 and one or more databases 220 operably coupled to a controller 203 over the network 230. The computer system 210 may be used for implementing the methods and systems consistent with those described elsewhere herein to improve the quality of live video in real-time. The computer system 210 may be used for implementing a live imaging enhancement system 211. The live imaging enhancement system 211 may comprise a training module configured to develop and train a deep learning framework using training datasets and a video enhancement module for executing the trained deep learning framework to perform inference. Although the illustrated diagram shows the controller and computer system as separate components, the controller and computer system (at least part of the live imaging enhancement system) can be integrated into a single component.

The imaging device 201 may acquire live video or image frames as described in FIG. 1. Live video or image frames may be streamed in using any medical imaging modality such as but not limited to CT, fMRI, SPECT, PET, ultrasound, etc. Image quality of the captured live video or image data stream may be degraded due to, for example, low temporal resolution or reduction in radiation dose or presence of noise in imaging sequence. The captured video stream may be low-quality such as low image resolution, low temporal resolution, low contrast, or low signal to noise ratio (SNR).

The controller 203 may be in communication with the imaging device 201, one or more displays and the live imaging enhancement system 211. The controller 201 may be operated to provide the controller information to manage the operations of the imaging system, according to installed software programs. For example, the controller 203 may control various components of the imaging system such as X-ray tube, spectral shaping filters, collimator, an anti-scatter grid, an image receptor (X-ray Image Intensifier), digital cameras based on charge-coupled device (CCD) image sensors or complementary metal oxide semiconductor (CMOS) technology, and various other post-image processing components.

In some cases, at least part of the live imaging enhancement system 211 may be integrated to the controller 203 or local to the controller such that video enhancement can be performed locally in real-time. In some cases, the live imaging enhancement system 211 may employ an edge intelligence paradigm such that inference or video enhancement may be performed at the edge or edge gateway (e.g., imaging system). In some instances, deep learning model may be built, developed and trained on a cloud/data center and run on the imaging system (e.g., hardware accelerator). For example, software that run on the edge may be the trained deep learning framework for processing the image stream in real-time. Software that run on the cloud or an on-premises environment may be the training module for training, developing, and managing the deep learning models.

The controller 203 may comprise or be coupled to an operator console which can include input devices (e.g., keyboard) and control panel and a display. For example, the controller may have input/output ports connected to a display, keyboard and other I/O devices. In some cases, the operator console may communicate through the network with a computer system that enables an operator to control the production (e.g., X-ray tube and image receptor) and display of live video on a screen of display. The live video displayed on the display may be processed by the live imaging enhancement system 211 and have improved quality.

The imaging platform 200 may comprise a user interface. The user interface may be configured to receive user input and output information to a user. The user input may be related to controlling or setting up a video acquisition scheme. For example, the user input may indicate radiation dose (e.g., radiation dose level), frame rate, desired radiation exposure level for each acquisition/run. The user input may be related to the video enhancement algorithm (e.g., sliding window size, estimated motion or property of a video, etc.) or desired enhancement parameters such as video smoothing level or sharpness level. The user interface may include a screen such as a touch screen and any other user interactive external device such as handheld controller, mouse, joystick, keyboard, trackball, touchpad, button, verbal commands, gesture-recognition, attitude sensor, thermal sensor, touch-capacitive sensors, foot switch, or any other device.

In some cases, the user interface may comprise a graphical user interface (GUI) allowing a user to select an operation mode, video displaying parameters, video enhancement parameters and image acquisition settings as described elsewhere herein. In some embodiments, the live imaging enhancement system 211 may allow for different operation modes. In some cases, the different operation modes may include a live video denoising mode, and a retrospective mode where a captured video is processed by the live imaging enhancement system 211 at a delayed time (e.g., after a complete video is captured or after at least part of the video is captured). The graphical user interface may allow a user to input user command to switch between the two operation modes.

The GUI may show graphical elements that permit a user to view or access information related to video enhancement or video display. A graphical user interface can have various interactive elements such as buttons, text boxes and the like, which may allow a user to provide input commands or contents by directly typing, clicking or dragging such interactive elements.

In some cases, the graphical user interface (GUI) or user interface may be provided on a display. The display may or may not be a touchscreen. The display may be a light-emitting diode (LED) screen, organic light-emitting diode (OLED) screen, liquid crystal display (LCD) screen, plasma screen, or any other type of screen. The display may be configured to show a user interface (UI) or a graphical user interface (GUI) rendered through an application (e.g., via an application programming interface (API) executed on the local computer system or on the cloud). The display may be on a user device, or a display of the imaging system as described in FIG. 1.

The live imaging enhancement system 211 may comprise multiple components such as a training module 213 configured to develop and train a deep learning framework using training datasets, and a video enhancement module 215 for deploying the trained deep learning framework and performing inferences. In some cases, the live imaging enhancement system may further be configured for continual training, generating and preparing training datasets, and managing deep learning models.

The training module 213 may be configured to train a deep learning model. In some embodiments, the training module may be configured to train a plurality of deep learning models assembled in a layered architecture for enhancing video quality in real-time. The training module may train the plurality of deep learning models individually. Alternatively or in addition to, the plurality of deep learning models may be trained as an integral model.

The training module 213 may be configured to generate and manage training datasets. For example, the training datasets for the real-time video enhancement may comprise pairs of low quality (e.g., low-dose) video and high quality (e.g., high-dose) video or 'ground-truth' video. High quality medical video datasets can be rare. Paired videos from the same subject can be even harder to collect. The provided training module may implement proprietary algorithm to simulate low-quality video and high-quality video to generate pairs of training datasets. For instance, video data taken under standard radiation dose (e.g., from clinical database) may be processed to generate high-quality video data simulating a high radiation dose (e.g., by applying temporal averaging and denoising to the standard video data). The same standard video data may also be processed to create a low-quality video data simulating low radiation dose by introducing artifacts to the video data such as by adding simulated noise scaled at different levels to the video data. Details about the process of generating training datasets and training method are described with respect to FIG. 5.

The training module 213 may be configured to train a deep learning network for enhancing the image quality. For example, the training module may employ supervised training, unsupervised training or semi-supervised training techniques for training the model. The training module may be configured to implement the machine learning methods as described elsewhere herein. The training module may train a model off-line. Alternatively or additionally, the training module may use real-time data as feedback to refine the model for improvement or continual training. Details about the training process and training methods are described later herein.

The video enhancement module 215 may be configured to enhance video quality in real-time using a trained model provided by the training module. The video enhancement module may implement the trained model for making inferences in real-time, i.e., producing image frames with improved quality. Details about the deep learning model architecture and model framework are described with respect to FIG. 3 and FIG. 4.

The computer system 210 may be programmed or otherwise configured to manage and/or implement the video enhancement module, training module and its operations. The computer system 210 may be programmed to implement methods consistent with the disclosure herein.

The imaging platform 200 may comprise computer systems 210 and database systems 220, which may interact with the live imaging enhancement system 211. The computer system may comprise a laptop computer, a desktop computer, a central server, distributed computing system, etc. The processor may be a hardware processor such as a central processing unit (CPU), a graphic processing unit (GPU), a general-purpose processing unit, which can be a single core or multi core processor, or a plurality of processors for parallel processing. The processor can be any suitable integrated circuits, such as computing platforms or microprocessors, logic devices and the like. Although the disclosure is described with reference to a processor, other types of integrated circuits and logic devices are also applicable. The processors or machines may not be limited by the data operation capabilities. The processors or machines may perform 512 bit, 256 bit, 128 bit, 64 bit, 32 bit, or 16 bit data operations.

The computer system 210 can communicate with one or more remote computer systems through the network 230. For instance, the computer system 210 can communicate with a remote computer system of a user or a participating platform (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 210 or the live imaging enhancement system via the network 230.

The imaging platform 200 may comprise one or more databases 220. The one or more databases 220 may utilize any suitable database techniques. For instance, structured query language (SQL) or "NoSQL" database may be utilized for storing video data, collected raw data, enhanced video data, training datasets, trained model (e.g., hyper parameters), user specified parameters (e.g., window size), etc. Some of the databases may be implemented using various standard data-structures, such as an array, hash, (linked) list, struct, structured text file (e.g., XML), table, JSON, NOSQL and/or the like. Such data-structures may be stored in memory and/or in (structured) files. In another alternative, an object-oriented database may be used. Object databases can include a number of object collections that are grouped and/or linked together by common attributes; they may be related to other object collections by some common attributes. Object-oriented databases perform similarly to relational databases with the exception that objects are not just pieces of data but may have other types of functionality encapsulated within a given object. If the database of the present disclosure is implemented as a data-structure, the use of the database of the present disclosure may be integrated into another component such as the component of the present disclosure. Also, the database may be implemented as a mix of data structures, objects, and relational structures. Databases may be consolidated and/or distributed in variations through standard data processing techniques. Portions of databases, e.g., tables, may be exported and/or imported and thus decentralized and/or integrated.

The network 230 may establish connections among the components in the imaging platform and a connection of the imaging system to external systems. The network 230 may comprise any combination of local area and/or wide area networks using both wireless and/or wired communication systems. For example, the network 230 may include the Internet, as well as mobile telephone networks. In one embodiment, the network 230 uses standard communications technologies and/or protocols. Hence, the network 230 may include links using technologies such as Ethernet, 802.11, worldwide interoperability for microwave access (WiMAX), 2G/3G/4G mobile communications protocols, asynchronous transfer mode (ATM), InfiniBand, PCI Express Advanced Switching, etc. Other networking protocols used on the network 230 can include multiprotocol label switching (MPLS), the transmission control protocol/Internet protocol (TCP/IP), the User Datagram Protocol (UDP), the hypertext transport protocol (HTTP), the simple mail transfer protocol (SMTP), the file transfer protocol (FTP), and the like. The data exchanged over the network can be represented using technologies and/or formats including image data in binary form (e.g., Portable Networks Graphics (PNG)), the hypertext markup language (HTML), the extensible markup language (XML), etc. In addition, all or some of links can be encrypted using conventional encryption technologies such as secure sockets layers (SSL), transport layer security (TLS), Internet Protocol security (IPsec), etc. In another embodiment, the entities on the network can use custom and/or dedicated data communications technologies instead of, or in addition to, the ones described above.

Deep Learning Framework

Figure 3:
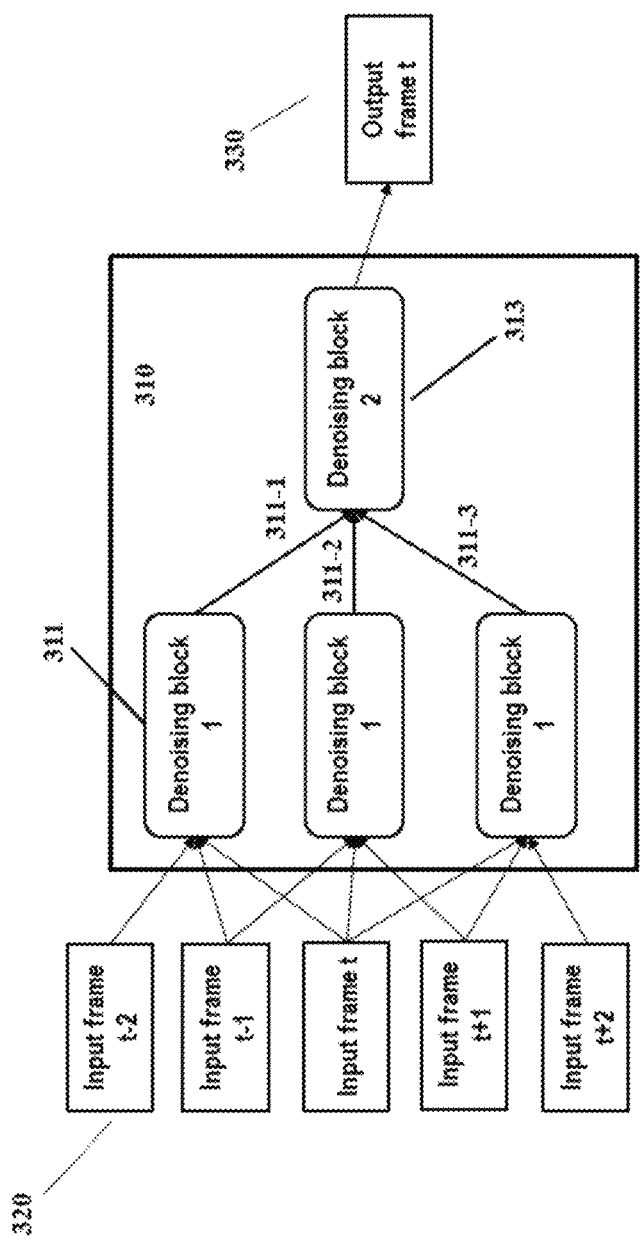
FIG. 3 schematically illustrates the architecture of the deep learning enhancement system, in accordance with some embodiments of the invention.

FIG. 3 schematically illustrates the architecture of the deep learning enhancement system 300, in accordance with some embodiments of the invention. The deep learning enhancement system 300 can be the same as the video enhancement module as described in FIG. 2. The deep learning enhancement system may comprise a trained deep learning model that is capable of improving live video quality. In some embodiments, the deep learning enhancement system may comprise a plurality of functional blocks assembled in a cascaded two-layer architecture. In some cases, each functional block may comprise a modified U-net model 311, 313. In some embodiments, the deep learning architecture may comprise a series of components are used to improve the input image frames quality (e.g., denoising video).

In some embodiments, the input of the deep learning framework 310 may comprise low-quality image data stream 320, and the output of the deep learning framework 310 may comprise an image frame with improved quality. In the illustrated example, a series of consecutive image frames 320 may be processed by the deep learning framework to generate an image frame 330 (e.g., estimation of the center frame of the series of input frames) with improved quality. Live video enhancement may be performed by leveraging intraframe information and interframe information. This unique architecture may beneficially allow for leveraging the inherent motion information by a built-in learning process without performing an additional, explicit motion estimation or compensation.

In some cases, the deep learning framework may comprise serialized functional blocks. For instance, a first layer of functional blocks (e.g., Denoising block 1) 311 may be used to process a series of consecutive image frames. The first layer of functional blocks may share the same weights. The series of consecutive image frames may be from an image stream or live imaging. The number of functional blocks or arrangement of the functional blocks of the first layer may depend on a sliding window size (e.g., number of consecutive image frames being processed in order to output one output image frame).

In some cases, each functional block 311 of the first layer may receive and process two or more consecutive image frames. For instance, for denoising a frame t, a first denoising block 1 311 may receive and process three adjacent image frames input frame t−2, input frame t−1, input frame t, and a second denoising block 1 may receive and process adjacent image frames input frame t−1, input frame t, input frame t+1.

The first layer of image frame enhancement may leverage temporal information across three image frames yielding a reduction of memory requirements of the model and facilitates the training of the network. The output of the functional blocks in the first layer may be intermediate image frames 311-1, 311-2, 311-3 with enhanced quality over the original input image frames. The quality of the intermediate image frames 311-1, 311-2, 311-3 may be enhanced in both the temporal and/or spatial domain compared to the quality of the series of input image frames. The first layer of functional blocks (e.g., Denoising block 1 311) may process a series of consecutive image frames substantially in parallel and the output of the first layer of functional blocks may comprise a series of improved image frames (e.g., triplet produced by the first layer) 311-1, 311-2, 311-3 to be processed by a functional block in a second layer, e.g., Denoising block 2 313. The intermediate frame (e.g., frame t−1, input frame t, input frame t+1) 311-1, 311-2, 311-3 corresponding to each functional block in the first layer may be different.

The second layer functional block may take the output of the first layer (e.g., intermediate frames 311-1, 311-2, 311-3) as input data and output image frame 330 (output frame t) with improved quality by leveraging the intraframe information of the series of input frames (input frame t−2, input frame t−1, input frame t, input frame t+1, input frame t+2) 311-1, 311-2, 311-3. In the illustrated example, the triplet (e.g., intermediate frames 311-1, 311-2, 311-3) composed by the outputs of the first layer Denoising blocks are used as inputs for the Denoising block 2 313 of the second layer. The output of the Denoising block 2 313 is the estimate of the central input frame (Input frame t) with a quality further improved other the intermediate frames.

In some embodiments, each component (e.g., Denoising block 1 311, Denoising block 1 313) may be a modified U-net architecture. As an example, the modified U-net may be a modified 16-layer U-net taking three adjacent frames as input. The plurality of denoising blocks may have the same modified U-net architecture but the weights may be different. For instance, after two steps of cascading denoising blocks, the network 310 may output a single denoised output frame t 330. The multiple denoising blocks in the first layer 311 may share the same set of weights which are different from the weights of the denoising block 313 in the second layer. In some cases, a different U-net architecture or number of layers may be selected with respect to different number of input frames. Alternatively, the architecture of the modified U-net may be the same regardless of the number of input frames. Details about the modified U-net architecture are described with respect to FIG. 4.

In some embodiments, the input image stream to be processed by the deep learning framework may be selected according to a property of the video, surgical operation, imaging modality and real-time conditions. In some embodiments, different sliding window sizes (of temporal neighboring frames) may be dynamically selected for different surgical operations, different time points during surgical operations and/or for different portions of an image frame (e.g., subset of pixels, patches in an image frame). For example, the sliding window size may be dynamically adjusted based on a motion estimation in the video. For instance, smaller window size may be selected when greater motion is detected to mitigate motion blur. In another example, a portion of an image frame (i.e., subset of pixels, patches) may be averaged over fewer adjacent consecutive images (i.e., smaller window size) if motion is detected within the location of the patch of the image frame. By requiring a small set of consecutive input frames (e.g., five frames) for inference, the denoising method is capable of running in a streaming fashion throughout the video acquisition process without delay.

The parameters for determining input data stream such as the sliding window size may be manually selected by a user or automatically adjusted. For instance, an algorithm for motion estimation such as DeepFlow, Farneback algorithm or LiteFlowNet may be applied to the live video to estimate motion at a point in time and/or location of patches within an image frame, then window size for processing the input image stream or a selected patch of the image frame may be automatically adjusted. In some cases, such dynamic adjustment and/or motion estimation is an inherent part of the deep learning architecture.

Figure 4:
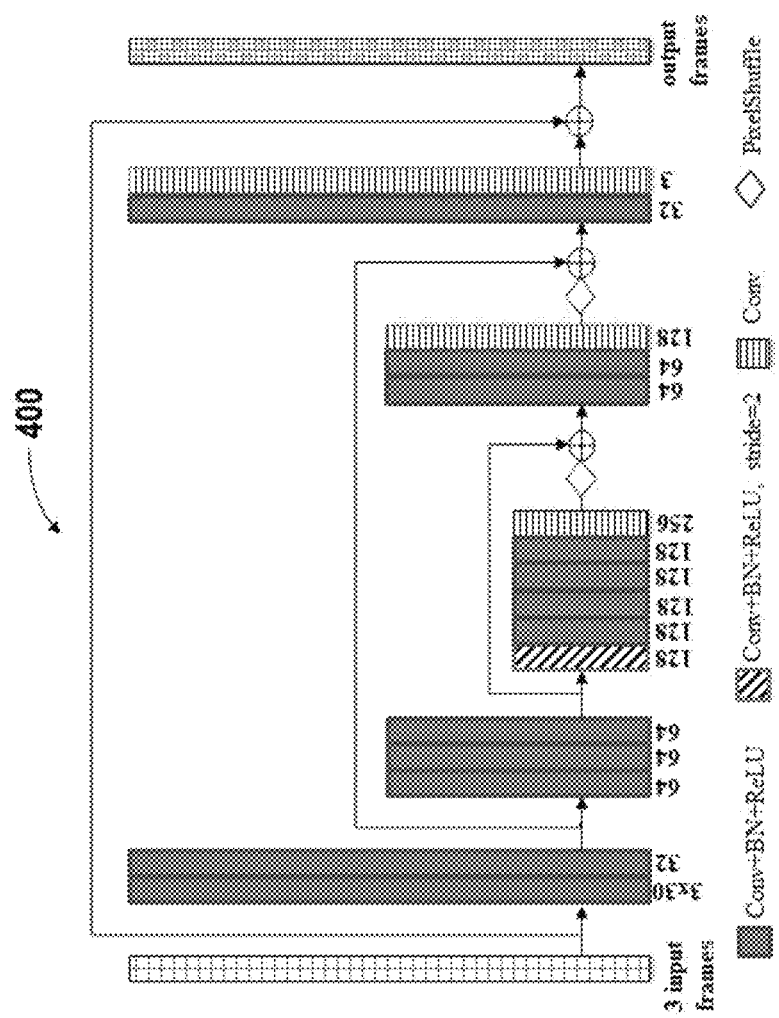
FIG. 4 shows an example of a modified U-net architecture employed by the deep learning model.

FIG. 4 shows an example of a modified U-net architecture 400 employed by the deep learning model. The U-net architecture 400 is essentially a multi-scale encoder-decoder architecture, with skip-connections that forward the output of each of the encoder layers directly to the input of the corresponding decoder layers. In the illustrated example of the modified U-net architecture, unsampling in the decoder is performed with a pixel shuffle layer which helps reducing gridding artifacts. The merging of the features of the encoder with those of the decoder is performed with pixel-wise addition operation resulting in a reduction of memory requirements. The residual connection between the central noisy input frame and the output frame is introduced to accelerate the training process. In some cases, each functional block or the denoising block may comprise a modified U-Net as described above.

The deep learning model can employ any type of neural network model, such as a feedforward neural network, radial basis function network, recurrent neural network, convolutional neural network, deep residual learning network and the like. In some embodiments, the deep learning algorithm may be convolutional neural network (CNN). The model network may be a deep learning network such as CNN that may comprise multiple layers. For example, the CNN model may comprise at least an input layer, a number of hidden layers and an output layer. A CNN model may comprise any total number of layers, and any number of hidden layers. The simplest architecture of a neural network starts with an input layer followed by a sequence of intermediate or hidden layers, and ends with output layer. The hidden or intermediate layers may act as learnable feature extractors, while the output layer may output the improved image frame. Each layer of the neural network may comprise a number of neurons (or nodes). A neuron receives input that comes either directly from the input data (e.g., low quality image data etc.) or the output of other neurons, and performs a specific operation, e.g., summation. In some cases, a connection from an input to a neuron is associated with a weight (or weighting factor). In some cases, the neuron may sum up the products of all pairs of inputs and their associated weights. In some cases, the weighted sum is offset with a bias. In some cases, the output of a neuron may be gated using a threshold or activation function. The activation function may be linear or non-linear. The activation function may be, for example, a rectified linear unit (ReLU) activation function or other functions such as saturating hyperbolic tangent, identity, binary step, logistic, arcTan, softsign, parameteric rectified linear unit, exponential linear unit, softPlus, bent identity, softExponential, Sinusoid, Sinc, Gaussian, sigmoid functions, or any combination thereof.

During a training process, the weights or parameters of the CNN are tuned to approximate the ground truth data thereby learning a mapping from low-quality video (e.g., low-dose video) to high-quality video (e.g., ground-truth video).

In the illustrated example, a functional block may comprise a plurality of convolutional layers. In most layers, the outputs of its convolutional layers are followed by pointwise ReLU activation functions ReLU(•)=max(•, 0), except for the last layer. At training time, batch normalization layers (BN) are placed between the convolutional and ReLU layers. At evaluation time, the batch normalization layers are removed, and replaced by an affine layer that applies the learned normalization.

Model Training and Development

In some embodiments, the deep learning model may be trained using supervised learning. For example, in order to train the deep learning network, pairs of videos with low quality (i.e., simulating videos taken under lower radiation dose) and high-quality videos as ground truth may be generated by the training module of the system as training dataset. The training datasets may comprise simulated low-quality video and high-quality video. For instance, video data taken under standard radiation dose (e.g., from clinical database) may be processed to generate high-quality video data simulating a high radiation dose (e.g., by applying temporal averaging and denoising to the standard video data). The same standard video data may also be processed to generate a low-quality video data simulating low radiation dose by introducing artifacts to the video data such as by adding noise scaled at different levels to the video data.

Figure 5:
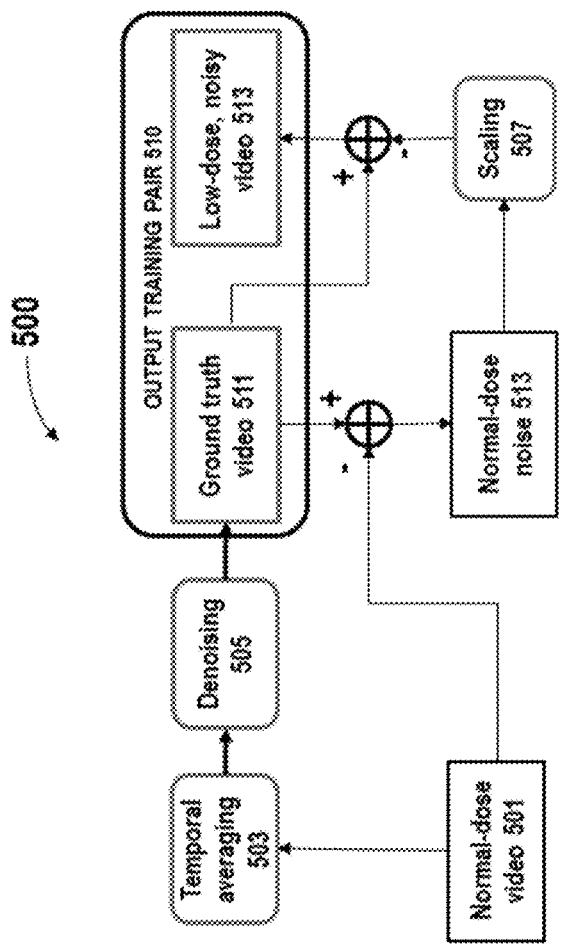
FIG. 5 schematically illustrates a method for generating training dataset, in accordance with some embodiments

FIG. 5 schematically illustrates a method 500 for generating training dataset, in accordance with some embodiments. The method may include obtaining an input video (operation 501). The input video may be a normal-dose video such as a video taken under a normal dose level. The input video may be obtained from a clinical database or other data sources.

The input video may then be temporally averaged across adjacent image frames (operation 503). In some cases, the temporal averaging operation may be adjusted based on a property of the input video. One or more parameters of the temporal averaging operation such as window size, pixel or spatial patches at the same location cross continuous image frame where the average operation to be applied may be dynamically adjusted. For instance, when the input video is still, the temporal averaging operation may be applied across all frames of the video and/or to the entire image frame. In other instances, when the input video contains motion, the temporal averaging operation may be adjusted to reduce the window size of adjacent image frame for averaging, and/or to apply the averaging to a subset of pixels or patches that are still. The temporal averaging parameters (e.g., sliding window size, patch or subset of pixels selected to be averaged over different number of adjacent frames) may be manually selected by a user or automatically adjusted. For instance, an algorithm for motion estimation such as DeepFlow, Farneback algorithm or LiteFlowNet may be applied to the input video to estimate motion in the video, then the window size for processing the input image stream or a selected patch of the image frame may be automatically adjusted based on the estimated motion. Alternatively, the temporal averaging parameters may be determined by a user according to a user-specified level of motion clarity.

Next, the video processed by the temporal averaging operation is further processed by a video denoiser (operation 505) to reduce noise in both spatial and temporal domain. In some cases, a video denoiser such as VBM4D video denoiser may be used for enhancing the video quality by mitigating artifacts such as noise, blur, blocking, or ringing. Other video filtering or denoising algorithms may also be used to enhance the video quality in both the spatial and temporal domain. After the denoising operation, the video may be high-quality (i.e., ground truth video 511) video simulating a video taken under high radiation dose.

The ground truth video 511 may be processed against the original input video 501 to create a low-quality video simulating a low-dose scenario. For instance, normal-dose noise 513 is obtained to approximate noise in the original input video by subtracting the normal dose video 501 from the ground truth video 511 such as by calculating the pixel-wise difference of the ground truth video and the original input video. This resulting difference pixel array may represent the coarse noise in the original input video 501 (e.g., normal-dose video).

The normal-dose noise 513 may then be scaled by a factor (operation 507) to simulate noise in a low-quality video. The factor may be a constant factor (e.g., at least 1.2, 1.5, 2, 2.5, 3, etc.) or a range of factors to simulate different levels of noise in low-quality videos. The constant factor or range of factors may be selected based on a physical relationship between the radiation dose level and a noise level. In some scenarios, the noise level may be linearly proportional to the radiation dose level. For example, the noise level may be inversely propositional to the square of level of radiation dose. Alternatively, the relationship between the radiation dose level and a noise level, or the range of factors may be obtained based on empirical data.

Next, the scaled noise may be added it to the ground truth video 511 to generate a low-quality video 513 simulating a video taken under low lose. The training dataset comprising the pair of ground truth video 511 and the low-quality video 513 may then be used for training the deep learning model or components of the deep learning framework (e.g., denoising block) individually. In some cases, different noise models (e.g., Gaussian i.i.d., etc.) may be selected to simulate noises for different imaging modalities or use cases.

In some embodiments, the deep learning model for enhancing video quality in real-time may be trained using supervised learning. Training datasets generated by the aforementioned method may be utilized to train the deep learning model or various components of the deep learning model. For example, the training dataset may comprise pairs of ground truth frame and a small set of noisy frames as described above. An example of the loss function for model training may be following:

$$\mathcal{L}(\theta) = \mathcal{L}_1(f_t^p, \hat{f}_t^p) = \|\hat{f}_t^p - \mathcal{F}(X_t^p;\theta)\|_1$$

Wherein $\widehat{f_t^p} = F(X_t;\theta)$ is the output of the network F parameterized by $\theta$. $f_t$ is the ground truth at time t, and $X_t = \{f_{t-2}, f_{t-1}, f_t, f_{t+1}, f_{t+2}\}$ which is a consecutive set of noisy, low-se frames. The patch index p may be a selected patch dimension. For example, the patch dimension may be 256×256 or any other number. The time index t corresponds to a frame chosen at random such that $2 < t \leq T-2$, wherein T is the total number of frames for a given sample. Note the L1 loss is an example of the loss function. Other loss functions such as SSIM or perceptual loss may be utilized in different scenarios.

In some embodiments, the deep learning model may be trained using unsupervised learning or semi-supervised learning that may not require abundant labeled data. High quality medical image datasets or paired dataset can be hard to collect. In some cases, the provided method may utilize unsupervised training approach allowing the deep learning method to perform continual training and apply on existing datasets (e.g., unpaired dataset) that are already available in clinical database. In some embodiments, the training process of the deep learning model may employ residual learning method. In some cases, the network structure can be a combination of U-net structure and a residual network.

In some embodiments, the model training process may further comprise operations such as model pruning and compression to improve inference speed. Model tuning may comprise deleting nodes of the trained neural network that may not affect network output. Model compression may comprise using lower precision network weights such as using floating point 16 instead of 32. This may beneficially allow for real-time inference (e.g., at high inference speed) while preserving model performance.

Example

Figure 6:
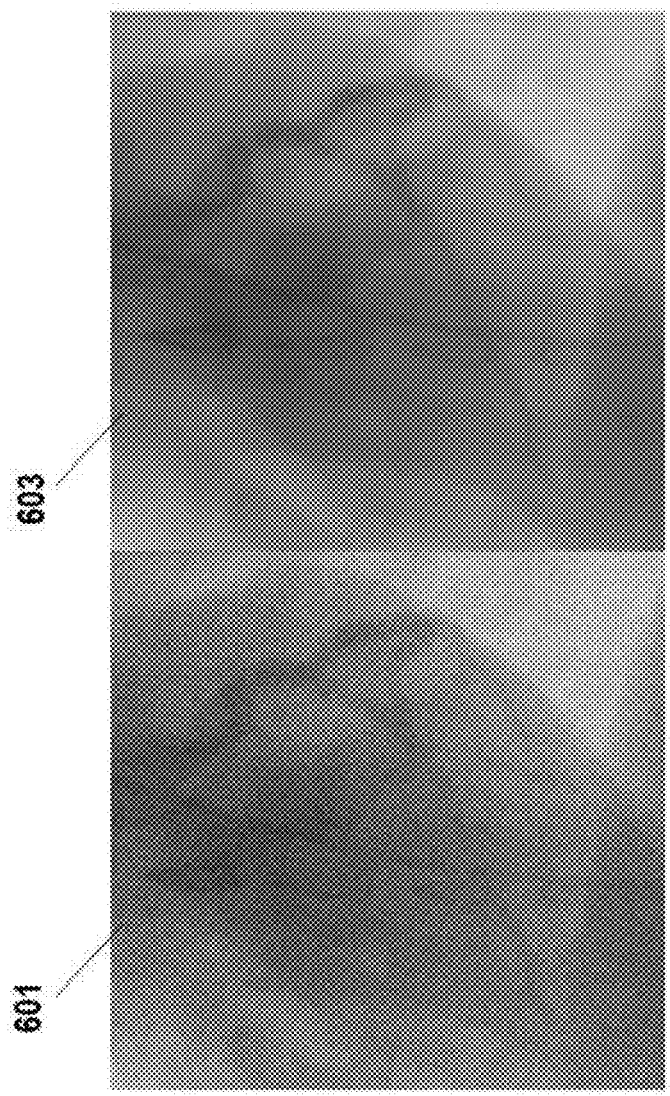
FIG. 6 shows an example of an image frame from a live video taken under low dose irradiation, and an improved image frame produced by the deep learning enhancement system.

FIG. 6 shows an example of an image frame from a live video taken under low dose irradiation 601, and an improved image frame 603 produced by the deep learning enhancement system. The improved image frame 603 has higher SNR and higher quality simulating an image frame acquired under higher radiation dose. The trained deep learning framework deployed in a clinical setting may perform inference in real-time. In the illustrated example, the trained deep learning framework is capable of enhancing video quality of a live video acquired at 30 frames per second, 1536×1536 image resolution and performing inference in less than 33.3 millisecond to avoid latency. After the additional operations such as model pruning and compression, the trained model network is capable of performing inference at speed of less than 12 millisecond. As described elsewhere herein, systems and methods of the present disclosure may perform real-time video enhancement to videos captured by a 4K camera or a camera with a higher resolution and at a frame rate of at least 25 frame per second.

Figure 7:
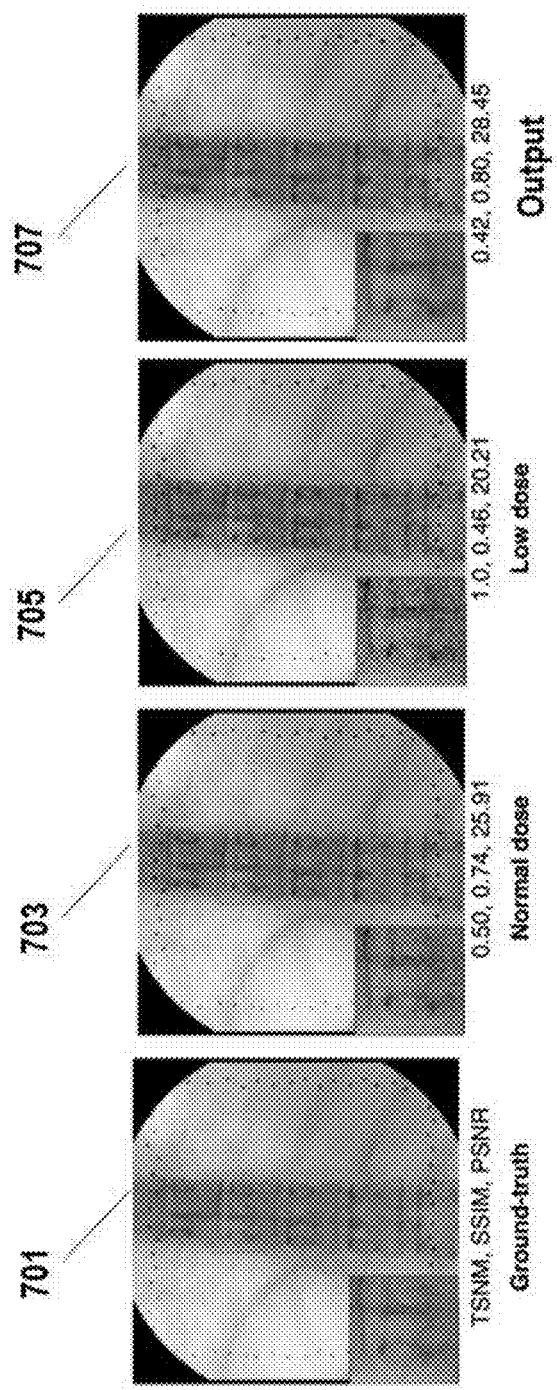
FIG. 7 shows an example of an improved image frame produced by the deep learning enhancement system.

FIG. 7 shows another example of an improved image frame 707 produced by the deep learning enhancement system. In an experiment, a live video acquired with 4× lower radiation dose 705 is processed by the deep learning enhancement system. The output video shows equal or better quality compared to the original normal-dose video 703 or the original low-dose video 705. In the experiment, the performance of the algorithm and/or the video quality is quantitatively evaluated using SSIM, PSNR, and a time-series noise metric (TSNM). Higher values for SSIM and PSNR correspond to higher quality which is measured in reference to the ground truth video sample 701. Because the metrics SSIM, PSNR are commonly used to evaluate image quality on a frame-by-frame basis without considering temporal information, the evaluation method of the present disclosure leverages TSNM which estimates noise in the spatiotemporal domain without relying on a ground-truth reference video. For example, a TSNM value of 0.5 corresponds to a 2× reduction in noise compared to the low-dose input.

As shown in the table below, when an input video with 4× lower dose is processed by the deep learning mechanism herein, the output video quality is improved compared to the normal-dose baseline.

|        | TSNM        | SSIM        | PSNR         |
|--------|-------------|-------------|--------------|
| Low-dose    | 1.0 ± .45   | 0.59 ± .14  | 25.16 ± 4.10 |
| Normal-dose | 0.52 ± .25  | 0.81 ± .10  | 31.40 ± 4.68 |
| Ours        | 0.29 ± .19  | 0.86 ± .07  | 32.58 ± 4.68 |
| VBM4D       | 0.64 ± .47  | 0.80 ± .10  | 29.18 ± 5.21 |

Additionally, the experiment also demonstrates a reduced runtime and faster inference. The dataset contains samples with frame rate varying between 4-30 frames per second (fps) and frame sizes of 768×768, 1024×1024, and 1536×1536 pixels. As shown in the table below, the runtime is significantly reduced enabling real-time video denoising.

| Frame size | Ours Runtime (ms) | Rate (fps) | VBM4D Runtime (ms) |
|------|----------------|-----|----------------|
| 384  | 6.27 ± 1.41    | 159 | 871.0 ± 134.7  |
| 768  | 21.53 ± 4.90   | 46  | 3625 ± 820.8   |
| 1024 | 37.46 ± 8.56   | 26  | 6857 ± 1330    |
| 1536 | 81.92 ± 18.88  | 12  | 8786 ± 1538    |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A computer-implemented method for improving live video quality comprising:
   (a) acquiring, using a medical imaging apparatus, a stream of consecutive image frames of a subject, wherein the stream of consecutive image frames is acquired with a reduced amount of radiation dose;
   (b) applying a deep learning network model to the stream of consecutive image frames to generate an output image frame with improved quality in both temporal domain and spatial domain, wherein the deep learning network model is trained using training datasets comprising a pair of a simulated low-quality video and a simulated high-quality video; and
   (c) displaying the output image frame with improved quality in real-time on a display.

2. The computer-implemented method of claim 1, wherein the simulated high-quality video is generated by applying a temporal averaging algorithm or a denoising algorithm to a video acquired with a normal radiation dose.

3. The computer-implemented method of claim 2, further comprising computing a noise based on a difference between the video and the simulated high-quality video.

4. The computer-implemented method of claim 2, further comprising applying a factor to the noise to simulate a level of noise corresponding to the factor.

5. The computer-implemented method of claim 4, wherein the simulated low-quality video is generated based at least in part on the level of noise and the simulated high-quality video.

6. The computer-implemented method of claim 1, wherein the deep learning network model comprises a plurality of denoising components.

7. The computer-implemented method of claim 6, wherein the plurality of denoising components are assembled in a two-layer architecture.

8. The computer-implemented method of claim 7, wherein each denoising component in a first layer of the two-layer architecture processes a subset of the stream of consecutive frames to output a series of intermediate image frames with an enhanced image quality.

9. The computer-implemented method of claim 8, wherein a denoising component in the second layer of the two-layer architecture processes the intermediate image frames with the enhanced image quality and generates the output image frame.

10. The computer-implemented method of claim 7, wherein each denoising component includes a modified U-net model.

11. The computer-implemented method of claim 10, wherein a denoising component in a second layer of the two-layer architecture has weights different from the weights of a denoising component in the first layer.

12. The computer-implemented method of claim 1, wherein the medical imaging apparatus is performing fluoroscopic imaging.

13. A non-transitory computer-readable storage medium including instructions that, when executed by one or more processors, cause the one or more processors to perform operations comprising:
   (a) acquiring, using a medical imaging apparatus, a stream of consecutive image frames of a subject, wherein the stream of consecutive image frames is acquired with a reduced amount of radiation dose;
   (b) applying a deep learning network model to the stream of consecutive image frames to generate an output image frame with an improved quality in both temporal domain and spatial domain, wherein the deep learning network model is trained using training datasets comprising a pair of a simulated low-quality video and a simulated high-quality video; and
   (c) displaying the output image frame with the improved quality in real-time on a display.

14. The non-transitory computer-readable storage medium of claim 13, wherein the simulated high-quality video is generated by applying a temporal averaging algorithm or a denoising algorithm to a video acquired with a normal radiation dose.

15. The non-transitory computer-readable storage medium of claim 14, wherein the one or more operations further comprise computing a noise based on a difference between the video and the simulated high-quality video.

16. The non-transitory computer-readable storage medium of claim 14, wherein the one or more operations further comprise applying a factor to the noise to simulate a level of noise corresponding to the factor.

17. The non-transitory computer-readable storage medium of claim 16, wherein the simulated low-quality video is generated based at least in part on the level of noise and the simulated high-quality video.

18. The non-transitory computer-readable storage medium of claim 13, wherein the deep learning network model comprises a plurality of denoising components.

* * * * *